United States Patent
Ungureanu et al.

(10) Patent No.: US 10,172,378 B2
(45) Date of Patent: Jan. 8, 2019

(54) MONO- OR BICYCLIC CARBOXYLIC ACIDS AS OFF-NOTE BLOCKERS

(71) Applicant: Givaudan, S.A., Vernier (CH)

(72) Inventors: Ioana Maria Ungureanu, Cincinnati, OH (US); Nicole Brune Servant, San Diego, CA (US); Jay Patrick Slack, Loveland, OH (US); Kimberley Gray, Loveland, OH (US); Christopher Todd Simons, Wyoming, OH (US); Jenny Ellen Evans Pennimpede, Cincinnati, OH (US)

(73) Assignee: Givaudan, SA, Vernier (CH)

( * ) Notice: Subject to any disclaimer, the term of this patent is extended or adjusted under 35 U.S.C. 154(b) by 0 days.

(21) Appl. No.: 15/084,199

(22) Filed: Mar. 29, 2016

(65) Prior Publication Data

US 2016/0205978 A1    Jul. 21, 2016

Related U.S. Application Data

(63) Continuation of application No. 12/669,393, filed as application No. PCT/CH2008/000332 on Jul. 28, 2008, now abandoned.

(60) Provisional application No. 60/962,514, filed on Jul. 30, 2007.

(51) Int. Cl.
  *A23L 1/22* (2006.01)
  *A23L 27/00* (2016.01)
  *A23L 27/30* (2016.01)

(52) U.S. Cl.
  CPC ........... *A23L 1/22075* (2013.01); *A23L 27/30* (2016.08); *A23L 27/84* (2016.08); *A23L 27/86* (2016.08); *A23V 2002/00* (2013.01)

(58) Field of Classification Search
  None
  See application file for complete search history.

(56) References Cited

U.S. PATENT DOCUMENTS

| | | | |
|---|---|---|---|
| 4,606,925 A | 8/1986 | Rohr et al. | |
| 4,786,332 A * | 11/1988 | Rohr | A24B 15/34 |
| | | | 131/276 |
| 6,592,924 B2 | 7/2003 | Blank et al. | |
| 7,273,623 B2 | 9/2007 | Kiel et al. | |
| 8,367,137 B2 | 2/2013 | Prakash et al. | |
| 2002/0028275 A1 | 3/2002 | Blank et al. | |
| 2003/0077321 A1* | 4/2003 | Kiel | A61K 9/2004 |
| | | | 424/465 |
| 2007/0116819 A1 | 5/2007 | Prakash et al. | |

FOREIGN PATENT DOCUMENTS

| | | | | |
|---|---|---|---|---|
| EP | 0 110 362 A | 6/1984 | | |
| EP | 1 013 177 A | 6/2000 | | |
| JP | 56-068612 | 6/1981 | | |
| JP | 1981-56068612 | * | 6/1981 | ............. A61K 31/19 |

OTHER PUBLICATIONS

STN Summary (Accession No. 1981:538635).*
Derwent Summary (Accession No. 1981-54184D).*
Summary entitled 'Novel Antiallergic Agent' (1981)).*
JAMA (vol. 58, p. 261 (1912)).*
Bazurin, Alexey A., et. al, "Improved synthesis of trans-4-alkylcyclohexane carboxylic acids", Tetrahedron Letters, Aug. 23, 2004, vol. 45, No. 5, pp. 6669-6672, Elsevier, Amsterdam, XP004556615.
Cheng, A. K., et. al, "$^{13}$C magnetic resonance studies 70. The behavior of bicyclo[2.2.2]octenone under strongly basic conditions. A competition between retro Diels-Adler and Haller-Bauer cleavages", Canadian Journal of Chemistry, Jun. 1977, vol. 55, pp. 4184-4190, London, Ontario, Canada, XP002510714.
Leopoldo, M., et. al, "First Structure-Activity Relationship Study on Dopamine D3 Receptor Agents with N-[4-(4-Arylpiperazin-1-yl)butyl]-arylcarboxamide Structure", Journal of Medical Chemistry, Dec. 15, 2005, vol. 48, No. 25, pp. 7919-7922, XP002510715.
PCT/CH2008/000332—Written Opinion of the International Searching Authority, dated May 2, 2009.
PCT/CH2008/000332—International Search Report, dated May 2, 2009.
Schubert, et al., "Liquid Crystals of Trans-4-n-alkylcyclohexanecarboxylic Acids", Zeitschrift fuer Chemie, 1972, pp. 219-220, vol. 12, Issue 6. English Abstract Only.

* cited by examiner

*Primary Examiner* — Craig D Ricci
(74) *Attorney, Agent, or Firm* — Curatolo Sidoti Co., LPA; Salvatore A. Sidoti; Floyd Trillis, III

(57) ABSTRACT

Disclosed are compounds that block off-notes in consumables and methods of blocking off-notes in consumables including off-notes provided by sweeteners such as stevioside, swingle extract, glyccerhizin, perillartine, naringin dihydrochalcone, neohesperidine dihydrochalcone, mogroside V, rubusoside, rubus extract, and rebaudioside A, and artificial sweeteners such as aspartame, saccharin, acesulfame K (Acesulfame potassium), sucralose and cyclamate.

4 Claims, No Drawings

Specification includes a Sequence Listing.

SEQUENCE LISTING

```
<160> NUMBER OF SEQ ID NOS: 4

<210> SEQ ID NO 1
<211> LENGTH: 1113
<212> TYPE: DNA
<213> ORGANISM: Artificial
<220> FEATURE:
<223> OTHER INFORMATION: recombinant sequence of rat/human/HSV
<220> FEATURE:
<221> NAME/KEY: CDS
<222> LOCATION: (1)..(1113)

<400> SEQUENCE: 1 atg gcc gct gtt acc tat cct tca tcc gtg cct acg acc ttg gac cct      48
Met Ala Ala Val Thr Tyr Pro Ser Ser Val Pro Thr Thr Leu Asp Pro
1               5                   10                  15
```

-continued

| | |
|---|---|
| ggg aat gca tcc tca gcc tgg ccc ctg gac acg tcc ctg ggg aat gca<br>Gly Asn Ala Ser Ser Ala Trp Pro Leu Asp Thr Ser Leu Gly Asn Ala<br>           20                    25                  30 | 96 |
| tct gct ggc act agc ctg gca gga ctg gct gtc agt ggc gaa ttc atg<br>Ser Ala Gly Thr Ser Leu Ala Gly Leu Ala Val Ser Gly Glu Phe Met<br>         35                    40                    45 | 144 |
| aca act ttt ata ccc atc att ttt tcc agt gtg gta gtg gtt cta ttt<br>Thr Thr Phe Ile Pro Ile Ile Phe Ser Ser Val Val Val Val Leu Phe<br>50                    55                    60 | 192 |
| gtt att gga aat ttt gct aat ggc ttc ata gca ttg gta aat tcc att<br>Val Ile Gly Asn Phe Ala Asn Gly Phe Ile Ala Leu Val Asn Ser Ile<br>65                    70                    75                  80 | 240 |
| gag cgg gtc aag aga caa aag atc tct ttt gct gac cag att ctc act<br>Glu Arg Val Lys Arg Gln Lys Ile Ser Phe Ala Asp Gln Ile Leu Thr<br>                    85                    90                    95 | 288 |
| gct ctg gcg gtc tcc aga gtt ggt ttg ctc tgg gta tta tta aat<br>Ala Leu Ala Val Ser Arg Val Gly Leu Leu Trp Val Leu Leu Leu Asn<br>                  100                 105                 110 | 336 |
| tgg tat tca act gtg ttt aat cca gct ttt tat agt gta gaa gta aga<br>Trp Tyr Ser Thr Val Phe Asn Pro Ala Phe Tyr Ser Val Glu Val Arg<br>               115                120                125 | 384 |
| act act gct tat aat gtc tgg gca gta acc ggc cat ttc agc aac tgg<br>Thr Thr Ala Tyr Asn Val Trp Ala Val Thr Gly His Phe Ser Asn Trp<br>130                 135                 140 | 432 |
| ctt gct act agc ctc agc ata ttt tat ttg ctc aag att gcc aat ttc<br>Leu Ala Thr Ser Leu Ser Ile Phe Tyr Leu Leu Lys Ile Ala Asn Phe<br>145                 150                 155                160 | 480 |
| tcc aac ctt att ttt ctt cac tta aag agg aga gtt aag agt gtc att<br>Ser Asn Leu Ile Phe Leu His Leu Lys Arg Arg Val Lys Ser Val Ile<br>                  165                 170                 175 | 528 |
| ctg gtg atg ctg ttg ggg cct tta cta ttt ttg gct tgt caa ctt ttt<br>Leu Val Met Leu Leu Gly Pro Leu Leu Phe Leu Ala Cys Gln Leu Phe<br>180                 185                 190 | 576 |
| gtg ata aac atg aaa gag att gta cgg aca aaa gaa tat gaa gga aac<br>Val Ile Asn Met Lys Glu Ile Val Arg Thr Lys Glu Tyr Glu Gly Asn<br>               195                200                205 | 624 |
| atg act tgg aag atc aaa ttg agg agt gca gtg tac ctt tca gat gcg<br>Met Thr Trp Lys Ile Lys Leu Arg Ser Ala Val Tyr Leu Ser Asp Ala<br>210                 215                 220 | 672 |
| act gta acc acg cta gga aac tta gtg ccc ttc act ctg acc ctg cta<br>Thr Val Thr Thr Leu Gly Asn Leu Val Pro Phe Thr Leu Thr Leu Leu<br>225                 230                 235                240 | 720 |
| tgt ttt ttg ctg tta atc tgt tct ctg tgt aaa cat ctc aag aag atg<br>Cys Phe Leu Leu Leu Ile Cys Ser Leu Cys Lys His Leu Lys Lys Met<br>                  245                 250                 255 | 768 |
| cag ctc cat ggt aaa gga tct caa gat ccc agc acc aag gtc cac ata<br>Gln Leu His Gly Lys Gly Ser Gln Asp Pro Ser Thr Lys Val His Ile<br>260                 265                 270 | 816 |
| aaa gct ttg caa act gtg atc ttt ttc ctc ttg tta tgt gcc gtt tac<br>Lys Ala Leu Gln Thr Val Ile Phe Phe Leu Leu Leu Cys Ala Val Tyr<br>               275                 280                 285 | 864 |
| ttt ctg tcc ata atg ata tca gtt tgg agt ttt ggg agt ctg gaa aac<br>Phe Leu Ser Ile Met Ile Ser Val Trp Ser Phe Gly Ser Leu Glu Asn<br>290                 295                 300 | 912 |
| aaa cct gtc ttc atg ttc tgc aaa gct att aga ttc agt tat cct tca<br>Lys Pro Val Phe Met Phe Cys Lys Ala Ile Arg Phe Ser Tyr Pro Ser<br>305                 310                 315                320 | 960 |
| atc cac cca ttc atc ctg att tgg gga aac aag aag cta aag cag act<br>Ile His Pro Phe Ile Leu Ile Trp Gly Asn Lys Lys Leu Lys Gln Thr | 1008 |

```
                     325                 330                 335
ttt ctt tca gtt ttg cgg caa gtg agg tac tgg gtg aaa gga gag aag    1056
Phe Leu Ser Val Leu Arg Gln Val Arg Tyr Trp Val Lys Gly Glu Lys
            340                 345                 350 cct tca tct cca tgc ggc cgc cag cct gaa ctc gct cct gaa gac ccg    1104
Pro Ser Ser Pro Cys Gly Arg Gln Pro Glu Leu Ala Pro Glu Asp Pro
        355                 360                 365 gaa gat taa                                                         1113
Glu Asp
    370

<210> SEQ ID NO 2
<211> LENGTH: 370
<212> TYPE: PRT
<213> ORGANISM: Artificial
<220> FEATURE:
<223> OTHER INFORMATION: Synthetic Construct

<400> SEQUENCE: 2

Met Ala Ala Val Thr Tyr Pro Ser Ser Val Pro Thr Thr Leu Asp Pro
1               5                   10                  15

Gly Asn Ala Ser Ser Ala Trp Pro Leu Asp Thr Ser Leu Gly Asn Ala
            20                  25                  30

Ser Ala Gly Thr Ser Leu Ala Gly Leu Ala Val Ser Gly Glu Phe Met
        35                  40                  45

Thr Thr Phe Ile Pro Ile Ile Phe Ser Ser Val Val Val Leu Phe
    50                  55                  60

Val Ile Gly Asn Phe Ala Asn Gly Phe Ile Ala Leu Val Asn Ser Ile
65                  70                  75                  80

Glu Arg Val Lys Arg Gln Lys Ile Ser Phe Ala Asp Gln Ile Leu Thr
                85                  90                  95

Ala Leu Ala Val Ser Arg Val Gly Leu Leu Trp Val Leu Leu Leu Asn
            100                 105                 110

Trp Tyr Ser Thr Val Phe Asn Pro Ala Phe Tyr Ser Val Glu Val Arg
        115                 120                 125

Thr Thr Ala Tyr Asn Val Trp Ala Val Thr Gly His Phe Ser Asn Trp
    130                 135                 140

Leu Ala Thr Ser Leu Ser Ile Phe Tyr Leu Leu Lys Ile Ala Asn Phe
145                 150                 155                 160

Ser Asn Leu Ile Phe Leu His Leu Lys Arg Arg Val Lys Ser Val Ile
                165                 170                 175

Leu Val Met Leu Leu Gly Pro Leu Leu Phe Leu Ala Cys Gln Leu Phe
            180                 185                 190

Val Ile Asn Met Lys Glu Ile Val Arg Thr Lys Glu Tyr Glu Gly Asn
        195                 200                 205

Met Thr Trp Lys Ile Lys Leu Arg Ser Ala Val Tyr Leu Ser Asp Ala
    210                 215                 220

Thr Val Thr Thr Leu Gly Asn Leu Val Pro Phe Thr Leu Thr Leu Leu
225                 230                 235                 240

Cys Phe Leu Leu Leu Ile Cys Ser Leu Cys Lys His Leu Lys Lys Met
                245                 250                 255

Gln Leu His Gly Lys Gly Ser Gln Asp Pro Ser Thr Lys Val His Ile
            260                 265                 270

Lys Ala Leu Gln Thr Val Ile Phe Phe Leu Leu Leu Cys Ala Val Tyr
        275                 280                 285

Phe Leu Ser Ile Met Ile Ser Val Trp Ser Phe Gly Ser Leu Glu Asn
```

```
                290                 295                 300

Lys Pro Val Phe Met Phe Cys Lys Ala Ile Arg Phe Ser Tyr Pro Ser
305                 310                 315                 320

Ile His Pro Phe Ile Leu Ile Trp Gly Asn Lys Lys Leu Lys Gln Thr
                325                 330                 335

Phe Leu Ser Val Leu Arg Gln Val Arg Tyr Trp Val Lys Gly Glu Lys
                340                 345                 350

Pro Ser Ser Pro Cys Gly Arg Gln Pro Glu Leu Ala Pro Glu Asp Pro
        355                 360                 365

Glu Asp
    370

<210> SEQ ID NO 3
<211> LENGTH: 45
<212> TYPE: DNA
<213> ORGANISM: herpes simplex virus

<400> SEQUENCE: 3
tgcggccgcc agcctgaact cgctcctgaa gacccggaag attaa              45

<210> SEQ ID NO 4
<211> LENGTH: 144
<212> TYPE: DNA
<213> ORGANISM: rat

<400> SEQUENCE: 4
atggccgctg ttacctatcc ttcatccgtg cctacgacct tggaccctgg gaatgcatcc    60
tcagcctggc ccctggacac gtccctgggg aatgcatctg ctggcactag cctggcagga   120
ctggctgtca gtggcgaatt catg                                          144
```

MONO- OR BICYCLIC CARBOXYLIC ACIDS AS OFF-NOTE BLOCKERS

CROSS-REFERENCE TO RELATED APPLICATIONS

The present application is a continuation of U.S. Ser. No. 12/669,393, filed Jan. 15, 2010, which is a national stage application of International Application No. PCT/CH2008/000332, filed Jul. 28, 2008, which claims the benefit of the filing date under 35 USC § 119(e) of U.S. Provisional Patent Application No. 60/962,514 filed on Jul. 30, 2007, which applications are incorporated herein by reference.

TECHNICAL FIELD

Disclosed are compounds that allow to mask or block undesirable off-notes in consumables and the method of blocking off-notes employing said compounds in consumables.

SUMMARY

Provided are the following:
(1) An off-note blocking compound of Formula (I)

$$\text{R1}\underset{\text{Cn}}{\overset{\text{R2, R2', R2'', R2'''}}{\diagup}}\overset{O}{\underset{OH}{\diagdown}} \quad (I)$$

wherein n is 0 or 1 (thereby forming cyclopentane or cyclohexane);
wherein the ring residue together with the dashed lines is selected from a cyclopentane residue (for n=0), a cyclohexane residue (for n=1), or a bicyclo[2.2.2]octane residue (with the dashed lines forming single bonds);
wherein for the cyclopentane and cyclohexane ring residues, R1 comprise a C3 to C10 alkane or arylalkane residue;
wherein for the bicyclo[2.2.2]octane residue, R1 comprises a C2 to C10 alkane or arylalkane residue;
wherein said R1 alkane or arylalkane residues are optionally selected from propyl, isopropyl, butyl, isobutyl, tertiary butyl, pentyl, isopentyl, hexyl, isohexyl, 2-methyl-hexyl, heptyl, isoheptyl, 2-methyl-heptyl, octyl, isooctyl, 2-methyl-octyl, nonyl, isononyl, 2-methyl-nonyl, decyl, isodecyl, 2-methyl-decyl, phenyl, tolyl and benzyl; wherein the number of carbon atoms in the residues of R1 and R2 together maximally is 12;
and wherein the optional ring substituents R2, R2', R2" and R2''' are each independently selected from H and methyl, or alternatively, instead of two of the methyl substituents, one cyclopropyl residue formed of two of the methyl residues R2-R2''' and a ring atom is present, or alternatively, instead of one of the methyl residues R2-R2''', a cyclopropyl residue formed of one of the methyl residues R2-R2''' and two ring carbon atoms may be present.
(2) The off-note blocking compound as described herein selected from one or more of cis-4-propylcyclohexanecarboxylic acid, cis-4-tert-butylcyclohexanecarboxylic acid, cis-4-propylbicyclo[2.2.2]octane-1-carboxylic acid, cis-4-sec-butylcyclohexanecarboxylic acid, cis-4-(4-methylpentyl)cyclohexanecarboxylic acid, cis-4-benzylcyclohexanecarboxylic acid, and cis-4-phenylcyclohexanecarboxylic acid.
(3) A flavor composition comprising an off-note providing consumable ingredient and one or more off-note blocking compounds of Formula (I).
(4) A consumable comprising
   a) at least one ingredient in a concentration sufficient to provide an off-note,
   b) one or more compounds off-note blocking compounds of Formula (I).
(5) A consumable as herein described wherein the off-note providing ingredient comprising one of sweeteners, artificial sweeteners, beverages, chewing gums, nutraceuticals, and pharmaceuticals.
(6) A consumable of as herein described wherein the off-note providing ingredient comprises one or more artificial sweetener selected from aspartame, acesulfame K, saccharin, sucralose, and sodium cyclamate.
(7) A consumable as herein described wherein the off-note providing ingredient comprises one or more sweeteners selected from stevioside, swingle extract, glyccerhizin, perillartine, naringin dihydrochalcone, neohesperidine dihydrochalcone, mogroside V, rubusoside, rubus extract, and rebaudioside A.
(8) A consumable as herein described wherein the off-note providing ingredient comprises a consumable selected from the group consisting of cocoa, coffee, caffeine, theobromine, diketopiperazines, vitamins, amino acids, vitamin B, casein, soy protein, ibuprofen, salicylic acid, glucoronolactone, acetaminophen, dextromethorphan, naringin, taurin, macrolide (including bioxin and erythomycin), paracetamol, acetylsalicylic acid, cimetidine, ranitidine, amoxicillin, acetominophen, cephalosporines, quassia, propylene glycol, triacetin, salts of potassium, salts of zinc, loperamide, limonin, flavonoides, isoflavones (including genistein and diadzein), polyphenol (including catechin and epicatechin), mint oil, D-menthol, hydrolysed vegetable protein, bitter peptides, preservatives (including benzoic acid, potassium sorbate, polysorbate 80, sodium and potassium lactate, sodium benzoate), citric acid, quinine, urea (contained in chewing gums), essential oils (including thyme, sage, basil, mint), Maillard reaction products (including cyclic amines made from pyrrolidine/glucose, alanine/xylose, proline/sucrose or alanine/xylose, for example diketopiperazines), beer, hops, humulone, trans-isohumulone, lupulone, and hulupone.
(9) A method of blocking off-notes in consumables comprising admixing with the consumable (a) at least one off-note providing ingredient in a concentration sufficient to provide an off-note, and (b) one or more off-note blocking compounds of Formula (I).
(10) A method as herein described wherein the off-note providing ingredient comprises selected one of sweeteners, artificial sweeteners, beverages, chewing gums, nutraceuticals, and pharmaceuticals.
(11) A method as herein described wherein the off-note providing ingredient comprises one or more artificial sweetener selected from aspartame, acesulfame K, saccharin, sucralose, and sodium cyclamate.
(12) A method of as herein described wherein the off-note providing ingredient comprises one or more sweetener selected from stevioside, swingle extract, glyccerhizin, perillartine, naringin dihydrochalcone, neohesperidine dihydrochalcone, mogroside V, rubusoside, rubus extract, and rebaudioside A.

(13) A method as herein described wherein the off-note providing ingredient comprises a consumable selected from the group consisting of cocoa, coffee, caffeine, theobromine, diketopiperazines, vitamins, amino acids, vitamin B, casein, soy protein, ibuprofen, salicylic acid, glucoronolactone, acetaminophen, dextromethorphan, naringin, taurin, macrolide (including bioxin and erythomycin), paracetamol, acetolsalicilic acid, cimetidine, ranitidine, amoxicillin, acetominophen, cephalosporines, quassia, propylene glycol, triacetin, salts of potassium, salts of zinc, loperamide, limonin, flavonoides, isoflavones (including genistein and diadzein), polyphenol (including catechin and epicatechin), mint oil, D-menthol, hydrolysed vegetable protein, bitter peptides, preservatives (including benzoic acid, potassium sorbate, polysorbate 80, sodium and potassium lactate, sodium benzoate), citric acid, quinine, urea (contained in chewing gums), essential oils (including thyme, sage, basil, mint), Maillard reaction products (including cyclic amines made from pyrrolidine/glucose, alanine/xylose, proline/sucrose or alanine/xylose, for example diketopiperazines), beer, hops, humulone, trans-isohumulone, lupulone, and hulupone.

DETAILED DESCRIPTION

The off-note blocking compound of Formula (I) provided herein include, without limitation, the following off-note blocking compounds: cis-4-propylcyclohexanecarboxylic acid, cis-4-tert-butylcyclohexanecarboxylic acid, cis-4-propylbicyclo[2.2.2]octane-1-carboxylic acid, cis-4-sec-butylcyclohexanecarboxylic acid, cis-4-(4-methylpentyl)cyclohexanecarboxylic acid, cis-4-benzylcyclohexanecarboxylic acid, and cis-4-phenylcyclohexanecarboxylic acid.

Their chemical structures are indicated below.

| Structure | Name |
|---|---|
| 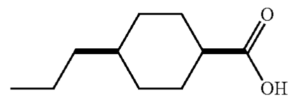 | cis-4-propylcyclohexanecarboxylic acid |
| 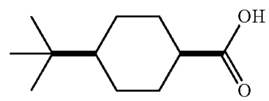 | cis-4-tert-butylcyclohexanecarboxylic acid |
| 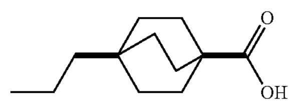 | cis-4-propylbicyclo[2.2.2]octane-1-carboxylic acid |
| 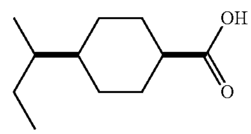 | cis-4-sec-butylcyclohexanecarboxylic acid |
| 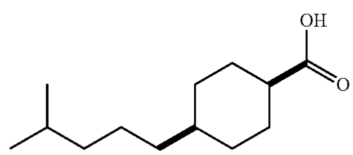 | cis-4-(4-methylpentyl)cyclohexanecarboxylic acid |
| 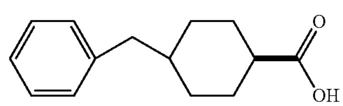 | cis-4-benzylcyclohexanecarboxylic acid |
| | cis-4-phenylcyclohexanecarboxylic acid | cis-4-propylcyclohexanecarboxylic acid, cis-4-tert-butylcyclohexanecarboxylic acid, cis-4-propylbicyclo[2.2.2]octane-1-carboxylic acid, cis-4-sec-butylcyclohexanecarboxylic acid, cis-4-(4-methylpentyl)cyclohexanecarboxylic acid, cis-4-benzylcyclohexanecarboxylic acid, and cis-4-phenylcyclohexanecarboxylic acid are either available commercially or can be synthesized as will be apparent to the skilled person.

cis-4-propylcyclohexanecarboxylic acid, cis-4-tert-butylcyclohexanecarboxylic acid and cis-4-sec-butylcyclohexanecarboxylic acid can be synthesized by hydrogenation of corresponding benzoic acid as will be apparent to the skilled person. cis-4-tert-butylcyclohexanecarboxylic acid also is commercially available from TCI America, Portland, Oreg., USA.

cis-4-propylbicyclo[2.2.2]octane-1-carboxylic acid is commercially available from AsInEx, Moscow, Russia.

cis-4-(4-methylpentyl)cyclohexanecarboxylic acid is commercially available from Sigma-Aldrich, St. Louis, Mo., USA.

cis-4-benzylcyclohexanecarboxylic acid can be synthesized by reducing cis-4-benzoylcyclohexane-1-carboxylic acid, and this starting material is available from Rieke Metals, Inc, Lincoln, Nebr., USA.

cis-4-phenylcyclohexanecarboxylic acid commercially available from ChemBridge, San Diego, Calif., USA.

All compounds of Formula (I) are either available commercially or can be synthesized easily by methods well known in the art, in particular hydrogenation, or as indicated herein.

A taste receptor screen and concentration-response analysis was performed and from results inhibitory concentration (IC) $IC_{50}$ values can be calculated by nonlinear regression using the function $f(x)=(a-d)/(1+(x/C)^{nh})+d$; with a=minimum signal, d=maximum signal, nh=hill coefficient, $C=IC_{50}$ and x=concentration of antagonist. $IC_{50}$ is the molar concentration of an antagonist which produces 50% of the maximum possible inhibitory response for that antagonist. A more potent antagonist will have a lower $IC_{50}$ value.

Most of the off-note blocking compounds disclosed herein, and in particular the compounds listed below, have an $IC_{50}$ in the range of about 0.1 to about 20 micromolar when tested with the TAS2R44 bitter taste receptor: cis-4-propylcyclohexanecarboxylic acid, cis-4-tert-butylcyclohexanecarboxylic acid, cis-4-propylbicyclo[2.2.2]octane-1-carboxylic acid, cis-4-sec-butylcyclohexanecarboxylic acid, cis-4-(4-methylpentyl)cyclohexanecarboxylic acid, cis-4-benzylcyclohexanecarboxylic acid, and cis-4-phenylcyclohexanecarboxylic acid For most food applications, a low $IC_{50}$ [micro molar] of about 0.05 to about 10 is desirable, however, $IC_{50}$ of about 10 to about 25 are still good and above about 25 may also still acceptable depending on the application.

Various food ingredients (including ingredients naturally contained in food or additives admixed to food including flavor ingredients) provide undesirable taste notes, so-called off-notes. Particularly undesirable off-notes are the bitter off-notes, metallic off-notes, lingering, licorice-type and astringent off-notes. The term off-note refers to an unpleasant after taste that develops over time after consumption of consumables.

Other particular examples are the bitter and/or metallic and/or astringent and/or "artificial" off-notes and/or a cloyingly sweet off-note (as opposed to the "cleaner" taste of sugar) that are associated with a number of artificial sweeteners including aspartame, acesulfame K, saccharin, sucralose, and sodium cyclamate. Sometimes these off-notes of artificial sweeteners are described collectively as bitter off-notes.

Further examples of off-note providing ingredients are naturally occurring sweeteners including stevioside, swingle extract, glyccerhizin, perillartine, naringin dihydrochalcone, neohesperidine dihydrochalcone, mogroside V, rubusoside, rubus extract, and rebaudioside A.

Still further examples of off-note providing ingredients include cocoa, coffee, caffeine, theobromine, diketopiperazines, vitamins, amino acids, vitamin B, casein, soy protein, ibuprofen, salicylic acid, glucoronolactone, acetaminophen, dextromethorphan, naringin, taurin, macrolide (including bioxin and erythromycin), paracetamol, acetolsalicylic acid, cimetidine, ranitidine, amoxicillin, acetominophen, cephalosporines, quassia, propylene glycol, triacetin, salts of potassium, salts of zinc, loperamide, limonin, flavonoides, isoflavones (including genistein and diadzein), polyphenol (including catechin and epicatechin), mint oil, D-menthol, hydrolysed vegetable protein, bitter peptides, preservatives (including benzoic acid, potassium sorbate, polysorbate 80, sodium and potassium lactate, sodium benzoate), citric acid, quinine, urea (contained in chewing gums), essential oils (including thyme, sage, basil, mint), Maillard reaction products (including cyclic amines made from pyrrolidine/glucose, alanine/xylose, proline/sucrose or alanine/xylose, for example diketopiperazines), beer, hops, humulone, trans-isohumulone, lupulone, hulupone.

The addition of off-note blockers will block or mask the off-notes and make them less apparent or unnoticeable. Artificial sweeteners will thereby lose their bitter/metallic taste and/or their cloyingly sweet lingering sweetness and instead taste more like actual sugar (sucrose).

Aspartame is the name for aspartyl-phenylalanine-1-methyl ester, a dipeptide. It is known under various trademark names including Equal®, and Canderel®. In the European Union, it is also known under the E number (additive code) E951.

Acesulfame potassium (AceK) is the potassium salt of 6-methyl-1,2,3-oxathiazine-4(3H)-one 2,2-dioxide, an N-sulfonylamide. It is also known as Acesulfame K or AceK, or under various trademark names including Sunett® and Sweet One®. In the European Union it is also known under the E number (additive code) E950.

Saccharin is the Na salt of 1,2-Benzisothiazol-3(2H)-one, 1,1-dioxide, an N-sulfonamide. It is also known under various trademark names including Sweet'n Low®.

Sucralose is the name for 6-dichloro-1,6-dideoxyl-β-D-fructo-furanosyl 4-chloro-4-deoxy-α-D-galactopyranoside, which is a chlorodeoxysugar. It is also known by the trade name Splenda®. In the European Union, it is also known under the E number (additive code) E955. Sucralose has an off-note (also designated "aftertaste") that is a lingering liquorice-like off-note sometimes also described as bitter.

The off-note blockers can be added to consumables to block the undesirable off-notes of ingredients present in said consumables or added to such consumables.

Flavor compositions for addition to consumables can be formed that provide the off-note blockers and an off-note providing ingredient for addition to consumables, and optionally food grade excipients. Alternatively, the off note blockers can be directly added to consumables.

In particular, the off-note blockers can be added to flavor compositions or directly to consumables to block the undesirable off-notes of off-note providing ingredients including natural and artificial sweeteners added to such consumables.

Consumables include all food products, food additives, nutraceuticals, pharmaceuticals and any product placed in the mouth including chewing gum, oral care products, and oral hygiene products including but not limited to, cereal products, rice products, tapioca products, sago products, baker's products, biscuit products, pastry products, bread products, confectionery products, desert products, gums, chewing gums, mouthwash, dental floss, flavored or flavor-coated straws, flavor or flavor-coated food/beverage containers, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, nutraceuticals, gelatins, pharmaceutical and non-pharmaceutical gums, tablets, lozenges, drops, emulsions, elixirs, syrups and other preparations for making beverages, and combinations thereof.

For example, in consumables containing salts of potassium, the off-note blocker may be added to suppress the bitterness and the metallic off-note associated with salts of potassium.

In coffee and cocoa products, the off-note blocker may be added to suppress the bitterness associated with caffeine, theobromine, and/or diketopiperazines present in said products.

In cheese products, in particular in enzyme-modified cheese products, the off-note blocker may be added to suppress the bitterness associated with bitter peptides present in said cheese products.

In soy products, the off-note blocker may be added to suppress the bitterness and beany off-notes associated with peptides, isoflavones such as genistein and diadzein present in said products.

In HVP (hydrolysed vegetable protein) products, the off-note blocker may be added to suppress the bitterness associated with bitter peptides present in said products.

In functional ingredients used in fortified foods, the off-note blocker may be added to suppress the bitterness associated with vitamins and amino acids present in said products.

In pharmaceuticals, the off-note blocker may be added to suppress the bitterness associated with actives or bitter additives present in said products.

In consumables containing solvents, the off-note blocker may be added to suppress the bitterness associated with propylene glycol, triacetin, or ethanol present in said products.

In citrus products, the off-note blocker may be added to suppress the bitterness associated with naringin present in said products.

In neutraceuticals and herb medicines, the off-note blocker may be added to suppress the bitterness associated with actives or additives present in said products.

In consumables containing polyphenols such as catechin and epicatechin, the off-note blocker may be added to suppress the bitterness associated with these ingredients.

In consumables containing preservatives such as potassium sorbate, polysorbate 80, sodium and potassium lactate, sodium benzoate, the off-note blocker may be added to suppress the bitterness associated with said preservatives.

In consumables containing zinc and other mineral supplements, the off-note blocker may be added to suppress the bitterness and metallic off-notes associated with said these mineral supplements.

In consumables containing mint oil or menthol (e.g. D-menthol) and citric acid of above 7%, the off-note blocker may be added to suppress the bitterness associated with this combination of ingredients.

In consumables containing quinine, the off-note blocker may be added to suppress the bitterness associated with quinine.

In consumables containing artificial sweeteners (e.g. aspartame, saccharin, acesulfame K, sucralose, cyclamate), for example beverages, a off-note blocker may be added to suppress the bitterness associated with artificial sweeteners.

In chewing gums, particular dental-type chewing gums, the off-note blocker may be added to suppress the bitterness associated with urea contained in chewing gums.

In consumables containing essential oils (e.g. thyme, sage, basil, mint), the off-note blocker may be added to suppress the bitterness associated with these essential oils.

In consumables containing vegetables or herbs or their extracts, the off-note blocker may be added to suppress the bitterness associated with these ingredients.

In consumables containing Maillard reaction products (i.e. cyclic amines made from proline/sucrose or alanine/xylose, e.g. diketopiperazines), the off-note blocker may be added to suppress the bitterness associated with Maillard reaction products.

In beer and consumables containing beer or hops, the off-note blocker may be added to suppress the bitterness associated with hops.

EXAMPLES

The following examples are set forth to describe the off-note blocking compounds in further detail and to illustrate the methods of employing the off-note blocking compounds to block or otherwise mask off-notes in consumables. The examples are illustrative and should not be construed as limiting the compounds, consumables or methods in any manner.

Example 1

Sensorial Evaluation in Various Consumables

Off-note blockers as herein described are tested by panels of 6 to 10 bitter sensitive panelists.

Panelists are asked to describe the differences in off-notes and bitter notes between the product with 0.001% (wt/wt) off-note blocker unless otherwise stated and a control without off-note blocker.

A) Aspartame/Acesulfame-K Containing Diet Energy Drink

The diet energy drink contained taurin, acesulfame K, aspartame, sucralose, glucuronolacton, caffeine, B-group vitamins (Niacin, pantothenic acid, B6, B12), aroma, sucrose, glucose, colours The sample containing the off-note blocker is found to be less bitter compared to the control.

B) Sucrose/Glucose-Sweetened Energy Drink

The diet energy drink contains taurin, glucuronolacton, caffeine, B-group vitamins (Niacin, pantothenic acid, B6, B12), aroma, sucrose, glucose, colours.

The sample containing the off-note blocker is found to have less off-notes, to be less bitter, and less astringent compared to the control.

C) Iced Low-Sugar Coffee

The sample containing the off-note blocker is found to be less bitter, and less astringent compared to the control.

D) Commercial Vanilla Flavored Nutritional Drink

Vanilla flavored nutritional drink containing calcium caseinate, soy protein isolate, sodium caseinate, vitamins and minerals.

The sample containing the off-note blocker is found to be less chalky, to have reduced protein/vitamin induced off-notes notes, and to be less astringent compared to control.

E) Saccharin Sweetened Cola Soft Drink

The sample containing the off-note blocker is found to be less bitter and to have a reduced after taste compared to the control.

F) Loperamide Containing Mint-Flavored Pharmaceutical Syrup

The syrup contained 1 mg loperamide HCl per 7.5 ml serving. The off-note blocker is used in a concentration of 0.004% (wt/wt).

The sample containing the off-note blocker is found to be less bitter with especially the lingering bitter after taste reduced.

G) Daytime Cough Syrup

The daytime cough syrup contains 325 mg acetaminophen, 10 mg dextromethorphan HBr, 5 mg phenylephrine HCl per 15 ml serving.

The sample containing the off-note blocker is found to be less bitter.

H) Dark Chocolate

The sample containing the off-note blocker is found to be less bitter.

I) Baking Chocolate (100% Cocoa, Unsweetened)

The off-note blocker is used in a concentration of 0.002% (wt/wt).

The sample containing the off-note blocker is found to be less metallic, less bitter, especially the alkaloid/caffeine-like bitterness is reduced while the upfront, warm, woody bitterness was retained.

J) Overcooked Coffee

Coffee is brewed and cooked on a burner for 3 hours. The off-note blocker is used in a concentration of 0.0005% (wt/wt).

The sample containing the off-note blocker is found to be less bitter.

K) Aspartame/Acesulfame-K Sweetened Plain Nonfat Yogurt

The yogurt contained 0.0193% (wt/wt) and acesulfame-K 0.0083% (wt/wt). The off-note blocker is used in a concentration of 0.00175% (wt/wt).

The sample containing the off-note blocker is found to have less off-notes compared to control.

L) Aspartame/Acesulfame-K Sweetened Cola Soft Drink

The off-note blocker is used in a concentration of 0.0063% (wt/wt).

| Cola soft drink | % (by weight) |
| --- | --- |
| Sodium Benzoate | 0.026 |
| Aspartame | 0.043 |
| Acesulfame-K | 0.017 |
| Caffeine | 0.011 |
| Phosphoric Acid (85%) | 0.043 |
| Citric Acid (50% cut in water) | 0.017 |
| Caramel Color | 0.085 |
| Water | Balance to 100 |

The sample containing the off-note blocker is found to have less off-notes than the control.

M) Sucralose Sweetened Cola Soft Drink

The off-note blocker is used in a concentration of 0.0035% (wt/wt).

| sucralose cola soft drink | % (by weight) |
| --- | --- |
| Sodium Benzoate | 0.03 |
| Sucralose (25% cut in water) | 0.06 |
| Caffeine | 0.01 |
| Phosphoric Acid (85%) | 0.08 |
| Caramel Color | 0.09 |
| Water | Balance to 100 |

The sample containing the off-note blocker is found to have less off-notes and be less bitter than the control.

Example 2

TAS2R44 Bitter Taste Receptor Assay for IC 50 Determination

1) Generation of Human TAS2R44 Expression Vector

The full length gene of human TAS2R44 was amplified by polymerase chain reaction (PCR) using gene-specific primers that span the entire coding region as described in WO 2004/029087.

The TAS2R44 cDNA was subcloned into an expression cassette based on either of the following plasmids/expression vectors: pcDNA3.1Zeo (Invitrogen). These vectors contain within their multiple cloning sites the nucleotide sequence coding for the first 45 amino acids of the rat somatostatin receptor subtype 3 (RSS tag) to facilitate cell surface targeting of the transgene (SEQ ID #4) and the nucleotide sequence coding for the herpes simplex virus (HSV) glycoprotein D epitope (HSV epitope in aminoterminal to carboxyterminal direction, HSV tag). (SEQ ID #3) for facilitating immunocytochemical detection.

The TAS2R44 construct contains RSS tag, TAS2R44, and the HSV tag which are fused in frame to allow translation into the receptor protein and the resulting receptor cDNA. This transfected expression vector is called pcDNA3.1Zeo-TAS2R44 (SEQ ID #1) and allows for expression of the TAS2R44 protein (SEQ ID #2).

2) Generation of a Cell Line Stably Expressing Gα16-Gustducin44 and TAS2R44

A cell line that stably expresses the human bitter taste receptor (TAS2R44) was generated by transfecting pcDNA3.1Zeo-TAS2R44 into HEK293T/Gα16-gustducin 44 cells (both formed as described in under 1) above). The host cell line HEK-293T is commercially available from the American Tissue Culture Collection (catalog #CRL-1573).

Transfection was Performed as Follows:

On day 0, the HEK293T Gα16-gustducin44 cells were seeded in a 6-well plate at a density of 900,000 cells per well and grown over night in selective growth medium (DMEM with 10% (v/v) heat-inactivated fetal bovine serum, 2 mM L-glutamine, 100 units/ml penicillin, 100 µg/ml streptomycin, 200 µg/ml G418 and 200 µg/ml zeocin). On day 1, the medium was exchanged with 2 ml of antibiotic-free and serum-free growth medium. 10 µl Lipofectamine 2000 was dissolved in 250 µl DMEM and incubated for 5 minutes at room temperature. In parallel, 4 µg TAS2R44 vector DNA were dissolved in 250 µl DMEM. These two resulting solutions are mixed and incubated for 20 minutes at room temperature before they are added to the cells into the cell culture medium. After 4 hours, the medium is replaced with antibiotic-free, serum-containing growth medium.

The cells were incubated in humidified atmosphere (37° C., 5% $CO_2$).

After 24 hours, the cells were re-plated in selective growth medium and were further incubated in a humidified atmosphere (37° C., 5% $CO_2$).

After 2 to 4 weeks of culture (replacing medium as necessary), zeocin-resistant colonies were selected and expanded.

The selected clone was tested successfully for functional expression of TAS2R44.

3) Fluo-4 Calcium Assay

Fluo-4_AM (Invitrogen) is a fluorescent indicator of intracellular calcium dynamics (change in concentration) and allows monitoring changes in the calcium concentration, particularly an increase in response to receptor activation occurring after agonist exposure.

At day 0, the HEK293T cell line stably expressing Gα16-gustducin44 and TAS2R44 formed as described under 2) was seeded in antibiotic-free growth medium (standard DMEM with 10% (v/v) heat-inactivated fetal bovine serum, 2 mM L-glutamine standard DMEM with 10% (v/v) heat-inactivated fetal bovine serum, 2 mM L-glutamine, 100 units/ml penicillin, and 100 µg/ml streptomycin) into black wall/clear bottom 96-well plates, coated with poly(ethylenimine) (0.005% v/v) at a concentration of 15,000 cells per well and incubated for 48 hours in humidified atmosphere (37° C., 5% $CO_2$).

At the time of the assay, the growth medium was discarded and the cells were further incubated in a humidified atmosphere (37° C., 5% $CO_2$) for 1 hour with 50 µl of loading buffer consisting of 1.5 µM Fluo-4 AM and 2.5 µM probenicid (Sigma-Aldrich) in DMEM.

Afterwards, the 96-well plate was washed 5 times with 200 µl of assay buffer (130 mM NaCl, 5 mM KCl, 10 mM HEPES, 2 mM $CaCl_2$, and 5 mM dextrose, pH 7.4) per well, using an automated plate washer (BioTek). The plate was further incubated for 30 minutes at room temperature in the dark to allow for complete de-esterification of the Fluo-4. Afterwards the plate was washed 5 times with 200 µl of assay buffer per well, and reconstituted with 180 µl of assay buffer per well.

For assay reading, the plate was placed in a Fluorometric Imaging Plate Reader (FLIPR) (FLIPR-TETRA™, Molecular Devices), and receptor activation was initiated by addition of 20 µl of a tenfold concentrated agonist stock solution (to give the desired agonist end concentration when added to the 180 microliter assay buffer volume), which was prepared in assay buffer.

Fluorescence was continuously monitored for 20 seconds to give a signal baseline (averaged to give $F_0$) prior to agonist addition and for 120 seconds after agonist addition. The change in signal divided by $F_0$ gives $\Delta F/F_0$ indicated in the table, with $\Delta F$ being the maximum signal occurring within the 120 seconds minus the minimum signal (occurring within the 120 seconds after agonist addition.

All data was collected from at least two independent experiments each carried out in triplicate.

A concentration-response analysis was performed and $IC_{50}$ values were calculated by nonlinear regression using the function $f(x)=(a-d)/(1+(x/C)^{nh})+d$; with a=minimum signal, d=maximum signal, nh=hill coefficient, $C=IC_{50}$, and x=antagonist concentration. $IC_{50}$ is the molar concentration of an antagonist which produces 50% of the maximum possible effective/inhibitory response for that antagonist. A more potent antagonist will have a lower $IC_{50}$ value.

The obtained calcium signals were corrected for the response of cells expressing only the G Protein a subunit (Gα16-gustducin44) and normalized to the fluorescence of cells prior to the stimulus using $\Delta F/F0$ (Fmax−Fmin/F0).

Example 3

Determination of IC50 of Off-Note Blockers

The following off-note blockers were tested: cis-4-propylcyclohexanecarboxylic acid, cis-4-tert-butylcyclohexanecarboxylic acid.

The method was performed as described in example 2, using saccharin as agonist.

The cells are exposed to a constant concentration of saccharin (0.5 mM) and to a set of different concentrations of the off-note blocker. A fluo-4 calcium assay was performed as described above in example 2 and gave an $IC_{50}$ [micro molar] within the range of 0.05 to 25.

This means that the off-note blockers inhibited the response of the TAS2R44 bitter taste receptor and will be useful to block bitter taste.

Example 4

Determination of IC50 for Off-Note Blockers

The method was performed as described in example 3, exchanging saccharin for Acesulfame K (0.8 mM) as agonist. An $IC_{50}$ within the same range was determined. This means that the off-note blockers inhibited the response of the TAS2R44 bitter taste receptor and will be useful to block bitter taste.

While the compounds, consumable and methods have been described above in connection with illustrative embodiments, it is to be understood that other similar embodiments may be used or modifications and additions may be made to the described embodiments for performing the same function without deviating therefrom. Further, all embodiments disclosed are not necessarily in the alternative, as various embodiments of the invention may be combined to provide the desired characteristics. Variations can be made by one having ordinary skill in the art without departing from the spirit and scope of the invention. Therefore, the compounds, consumables and methods should not be limited to any single embodiment, but rather construed in breadth and scope in accordance with the recitation of the attached claims.

The invention claimed is:

1. A flavor composition comprising:
one or more off-note providing ingredients in a concentration sufficient to provide a flavor and one or more undesirable off-notes, wherein said one or more undesirable off-note providing ingredients comprises one or more artificial sweeteners; and
an off-note blocking compound comprising cis-4-tert butylcyclohexanecarboxylic acid in a concentration of about 0.001 to about 0.006 weight % based on the weight of the off-note providing ingredients and the off-note blocking compound to block or mask said undesirable off-notes of said one or more off-note providing ingredients.

2. A consumable comprising:
at least one selected from a food product, a food additive, a beverage, a chewing gum, an oral care product, an oral hygiene product, a pharmaceutical, or a nutraceutical; and
one or more off-note providing ingredients in a concentration sufficient to provide a flavor and one or more undesirable off-notes, wherein said one or more undesirable off-note providing ingredients comprises one or more artificial sweeteners; and
an off-note blocking compound cis-4-tert butylcyclohexanecarboxylic acid in a concentration of about 0.001 to about 0.006 weight % based on the weight of the off-note providing ingredients and the off-note blocking compound to block or mask said undesirable off-notes of said one or more off-note providing ingredients.

3. A flavor composition comprising:
one or more off-note providing ingredients in a concentration sufficient to provide a flavor and one or more undesirable off-notes, wherein said one or more off-note providing ingredients comprises one or more naturally occurring sweeteners; and
an off-note blocking compound comprising cis-4-tert butylcyclohexanecarboxylic acid in a concentration of about 0.001 to about 0.006 weight % based on the weight of the off-note providing ingredients and the off-note blocking compound to block or mask said undesirable off-notes of said one or more off-note providing ingredients.

4. A consumable comprising:
at least one selected from a food product, a food additive, a beverage, a chewing gum, an oral care product, an oral hygiene product, a pharmaceutical, or a nutraceutical; and
one or more off-note providing ingredients in a concentration sufficient to provide a flavor and one or more undesirable off-notes, wherein said one or more off-note providing ingredients comprises one or more naturally occurring sweeteners; and an off-note blocking compound comprising cis-4-tert butylcyclohexanecarboxylic acid in a concentration of about 0.001 to about 0.006 weight % based on the weight of the off-note providing ingredients and the off-note blocking compound to block or mask said undesirable off-notes of said one or more off-note providing ingredients.

* * * * *